(12) United States Patent
Shao et al.

(10) Patent No.: US 6,987,020 B1
(45) Date of Patent: Jan. 17, 2006

(54) FULL-GENE SEQUENCE OF THE DONKEY LEUKOCYTE VACCINE STRAIN OF THE EQUINE INFECTIOUS ANEMIA VIRUS AND THEIR APPLICATION

(75) Inventors: Yiming Shao, Beijing (CN); Rongxian Shen, Heilongjiang (CN); Gang Chen, Beijing (CN); Kangzhen Yu, Heilongjiang (CN); Pinliang Pan, Beijing (CN); Bin Jia, Heilongjiang (CN); Yi Feng, Beijing (CN); Fel Xue, Heilongjiang (CN); Wenhua Xiang, Heilongjiang (CN); Xiujuan Fan, Beijing (CN); Xieoling Lu, Heilongjiang (CN); Liping Zhao, Heilongjiang (CN)

(73) Assignees: National Center for Aids Prevention and Control, Beijing (CN); Harbin Veterinary Research Institute, Chinese Academy of Agriculture Science, Heilongjiang Province (CN)

( * ) Notice: Subject to any disclaimer, the term of this patent is extended or adjusted under 35 U.S.C. 154(b) by 0 days.

(21) Appl. No.: 09/959,120

(22) PCT Filed: Apr. 21, 2000

(86) PCT No.: PCT/CN00/00096

§ 371 (c)(1),
(2), (4) Date: Jan. 3, 2002

(87) PCT Pub. No.: WO00/63387

PCT Pub. Date: Oct. 26, 2000

(30) Foreign Application Priority Data

Apr. 21, 1999 (CN) .............................. 99105852 A

(51) Int. Cl.
*C12N 15/00* (2006.01)
*C12N 15/63* (2006.01)
*C07H 21/04* (2006.01)

(52) U.S. Cl. ................................ 435/320.1; 536/23.72
(58) Field of Classification Search ............. 424/207.1, 424/204.1, 93.2; 435/5, 91.32, 91.33, 235.1, 435/320.1; 536/23.1, 23.72
See application file for complete search history.

(56) References Cited

FOREIGN PATENT DOCUMENTS

| CN | 1134458 | 10/1996 |
|----|---------|---------|
| WO | WO 92/00987 | 1/1992 |
| WO | WO 97/39119 | 10/1997 |
| WO | WO 98/51810 | 11/1998 |
| WO | WO 99/35273 | * 7/1999 |

OTHER PUBLICATIONS

Shen et al. Development and use of an equine infectious anemia donkey leukocyte attenuated vaccine. 1985. In: R.J. Tashjian editor. Equine Infectious Anemia. Amarillo, TX: American Quarter Horse Association. pp. 135-148.*
Rasty et al. Journal of Virology. 1990; 64 (1): 86-95.*
Liu et al. Science in China Series C Life Sciences. Feb., 2002; 45 (1): 57-67.*
Zhou et al. Veterinary Microbiology. 2002; 88: 127-151.*
Kaplitt et al. 1995. Viral Vectors. Academic Press, Inc. San Diego, CA; pp. 215-216, and 229.*

* cited by examiner

Primary Examiner—Shanon Foley
(74) Attorney, Agent, or Firm—Nixon & Vanderhye P.C.

(57) ABSTRACT

This invention discloses the full-length proviral genome DNA sequence of Donkey Leukocyte Attenuated Equine Infectious Anemia Virus Vaccine strain, nucleotide and amino acid sequences of all functional genes, and uses of each functional gene and its expression product. The vaccine strain involved in this invention was derived from an isolate in China.

3 Claims, 2 Drawing Sheets

1    2    3    4

1    2    3    4    5

SEQUENCE LISTING

<160> NUMBER OF SEQ ID NOS: 39

<210> SEQ ID NO 1
<211> LENGTH: 8258
<212> TYPE: DNA
<213> ORGANISM: Equine Infectious Anemia Virus (EIAV)

<400> SEQUENCE: 1

```
tgtggggttt ttatgagggg ttttataaat gattataaga gtaaaaagaa ggggggctgat      60 gctctcataa ccttgtataa cccaaggac tagctcatgt tgctaggcaa ctaaaccgca       120
atatcctgta gttcctcttg cgttccgcat ttgtgacgtt ttaagttcct gttttttacag    180 tatataagtg cttgtattct gacaattggg cactcagatt ctgcggtctg agtcccttct    240
ctgctgggct agactagcct ttgtaataaa tataattctc tgctaagtcc ctgtctctag    300
tttgtcttgt tttcaagatc taacagctgg cgcccgaaca gggacctgag ggcgcagacc    360
ctgcctgctg aacctggctg atcataggat ccctaggaca gcagaggaga acttacagaa   420
gtcttctgga ggtgttcctg gccacaacac aggaagacag gtaagatggg agactctttg   480
acatggagca aagcgctcaa gaagttagag aaggtgacgg tacaagggtc tcaaaagcta   540
actagtggta actgtaattg ggcgctgaat ttggtggact tattccatga caccaatttt   600
ggtaaagaaa aagactggca attaagggac gtcattccat tgttagagga cgtttcccag   660
```

```
acgttgtcag gacaagagag agaggcattt gaaaaaactt ggtgggcaat agctgccgtt      720
aagatgggct tacaaattaa tactgtgaat gatgcaaaaa caacattttc tatattaaaa      780
gccaagtttg aaagaaagac tgcaaataat accaaaaagc agtctgagcc cgaggaagaa      840
tacccaataa tgattgatgg ggctggaaac agaaactttc ggccattaac acccagagga      900
tatactacct gggtaaatac tatacagcaa acaatctct  taaatgaagc tagtgtgaat      960
ttatttggta ttttatcagt agactgtact tctgaggaaa tgaatgcatt tttggatgta     1020
gtaccaggac aagcaggaca aaacaagta  ctattggata tcttgataaa gattgcagaa     1080
gaatgggatc gtaggcaccc gttgccaaat cctccattag tggcaccacc acaagggcct     1140
attcccatga cagcaaggtt cattagggga ttgggagttc ctagagaaag acagatgaaa     1200
cctgcttttg atcagtttag acaaactat  agacaatgga atagaagc   aatgacagaa     1260
gggataaaaa taatgattgg gaaacccaaa gcgcaaaata ttaggcaagg acccaaagaa     1320
ccctatccag agtttataga cagattgctg tctcagataa aaagtgaggg catccggct      1380
gatataacta aattcctgac agacacttta actattcaga atgctaatga tgaatgcaaa     1440
aatgctatga gacatttgag gccagaagat actttagaag agaaaatgta tgcatgtaga     1500
gatattggca ctatgagaca aaaaatggca ttattagcca aggcacttca agcaggatta     1560
gctggtccta tgaagggagg aatatttaaa gggggaccct taggggcgaa gcagacatgt     1620
tataattgtg gaaaaccagg acattttct  agtcaatgta aagcacctaa aatatgtttt     1680
aagtgcaaac agccaggaca tttctcaaaa caatgtataa atgctccaaa aaacgggaaa     1740
caagggctc  aggggaggcc ccagaaacaa actttccctg tgcagaagga gtcaatgaac     1800
aaaacacaaa aagaggagaa acagcaaggg accttatatc cagatttaag tcagatgaaa     1860
caggaataca agatcaagga agaggaaaat caagaggatc tcaatctgaa cagtttgtgg     1920
gagtaactta taatttagaa aagagaccaa ctacaatagt cttgattaat gacacaccct     1980
taaatgtatt gttggacaca ggagcagaca catcagtact aactattgca cattgtaata     2040
ggttaaagta tggaggaaga aaatatcaag gtacaggtat tgttggggtt ggaggtaatg     2100
tagaaacatt ttccactcct gttacagtga aaagaaagg  aaaacaaatt aaaactagaa     2160
tgttagtagc agatatccca gttactattt tggggcgaga tattcttcaa gaattaggcg     2220
cacaattact aatggctcaa ctttcaaaag aaataacccc aagagaaatt aaattaaaaa     2280
caggcacagt agggcctaag gttccccaat ggccacttac taaagagaag ttgttaggtg     2340
ctaaagaaat agtcaaaaaa ttgttggatg aaggtaaaat atcagaagcc agtgatgata     2400
atccttataa ttctcctata tttgtaataa aaaagaaatc tggaaagtgg agattattgc     2460
aagatttaag agagttaatt aagggtggta caagtagaac tgaaatatcc agaggattac     2520
ctcatccagg gggattaatt aaatgtaatc atatgacagt attagatatt ggagatgcat     2580
atttcactat accattagat ccaaagttta gacaatatac agcatttact gtgccatcca     2640
ttaatcatca ggaaccagat aaaagatatg tgtggaattg cttgccacaa ggttttgtgt     2700
taagtccata catatatcaa aaaacattac aggacatatt acaagctttt agagaaaggc     2760
atccagatgt acaattatat caatatatgg atgatttatt cattgggagt aatgaatcta     2820
aaagacaaca taaggaacta gtagaagaat taagagctat tctttttagaa aagggctttg     2880
agacgcctgg ggataaattg caggaagaag cacccctata ttggctggga tatcaactta     2940
gtccaggcaa ttggaaagta caaagatgc  aattagaatt ggtaaaagag ccaacattaa     3000
```

-continued

```
atgatgtgca aaaatcaaag ggaaatataa catggatgag ctcagggggtt cctggattaa      3060 cagtgaagca aatagctgct accactaaag gttgcttaga tttaaatcat aaaggtagta      3120
ggaccagaga agcccaaaaa gacttagagg aaattattaa agtttcaga agctcaggat       3180 tcccatatta taacccagaa gaagaagtaa tctgtgagat tgaaattact aaaaattatg     3240
aggctactta tataataaaa cagtctcaag gaatattgtg ggcaggaaag aaaattatga     3300
gggctaataa aggatggtcc gcagcaaaaa atcaatgtt attgttacaa catgtagcca      3360
cagaaagtat tgttagaatt ggaacatgtc caaaatttaa agtaccttt actaaagaac      3420 aagtcaaatg ggaaatggaa aagggatggt attattcatg gctaccagac atggtatatt    3480
cacatcaagt tgttcatgat gattggagac tgaaattagt agagcaacca acatctggta   3540
taacaattta tactgatggg ggtaaacaga atgaagaagg agttgcagct tatgtgacta    3600
gtaatgggaa aactaaacaa aaaaggttag ggcctgttac tcatcaaact gctgagagga   3660
tagcaataca aatggcatta gaagatactg aagagacatt ggtaaatata gtaactgata   3720
gttactactg ttggaaaaat attacagaag gattagggtt agaaggacca gacagcccct    3780
ggtggccaat aattcaaaat attagggcta agaaatggtt ttatttttgct tgggtaccag   3840 gtcacaaagg aatatatggc aatcaattgg cagatgaggc tactaaaata acagaggaaa    3900
ttatgttagc atatcaaggc acacagatta gggaaaaaag agatgaagat gcagggtatg   3960
atttgtgtat tccttatgac ataatgatac ctgtctctga caaaagtt atacccacag      4020 atgtaaaaat acaggtacct cacaaatgtt tggatgggt aactggtaag tcatcaatgg     4080
ctaagcaagg attattaatc aatggggggaa taattgatga aggatacaca ggtgaaatac  4140
aggtaatttg tactaatatt ggaaagagta acatgaaact cagggaagga caaaagtttg   4200
cacaattaat catattacag catcgatcaa atgataaaca aatctgggat gaaaataaaa  4260
catctcaaag gggagataaa gggttttgaa gcacaggtat attttgggta gagaatatcc   4320
aagaggcgca agatgaacat gaaaattggc atacatctcc aaagatattg gcaaaaagat  4380
atgggttacc attgactgta gctaaacaga taactcaaga atgccctcat tgtactaaac  4440
aaggatctgg accagcaggt tgtgtaatga gatctcctaa tcattggcag gctgattgta  4500
cacatttaga aaacagggta ataatgacat ttgtagagtc taattcagga tacattcatg  4560
ctactctatt gtccaaagaa aatgccttgt gtccttcatt ggctatttg gaatgggtga    4620 ggttattttc tcctaaatct ttacatacag acaatggtac taattttgtg gcagagtcag  4680
tagcaaatct gttgaaattc ctgaaggtga cacatactac aggaatacct tatcacccag   4740
agagccaagg cattgtggaa agagcaaaca ggacattaaa agaaagaatt aaaagtcata   4800
gaggaaatac tcagacactt gaagcagcat tacaacttgc tctcattact tgtaacaaag    4860
ggagggaaag tatgggagga caaactccat gggaagtatt tattactaat caggctcaaa   4920
caatacatga agaactttta ttacaacaag cacaatcttc taaaaaattt tgttttttata  4980 aaattcctgg tgagcataat tggaagggc ccaccagagt gttgtggaaa ggtgatggag     5040
cagtagtggt caatgatgag gaaaaaggaa taattgctgt gccttaacc aggactaaat    5100 tattaataag accaaattga gcattgtttc aggaatcacc accagtcagc tatcattgtc   5160
aactgtgttt cctgagatca ttgggaattg actaccttga cagctcgctg aagaagaaga  5220
acaaacaaag acagaaggcc atcagggagg aagacaacct cagtatcttg ttataaggtt    5280
tggtgtatgg gattatttgg taagggggta acatggtcag cattcattc tatgggggta   5340 tcccaggggg aatatcaacc cctatcaccc aacaaacaga atcaacagac acacagaaag  5400
```

-continued

```
gggatcatat ggtatatcaa ccctattgtt ataatgatag ccataaagaa gaaatggcag    5460
agacaagaga cacaagatac caagaagaaa tgaaccggaa agaagataaa gaagataaaa    5520
gaaagaataa ctggtggaag ataggtatgt tcttattgtg tctgttagag atcactggag    5580
gattcctctg gtggtatgag aggcaacaac attcatatta tataagattg gttacaatag    5640
gaggtagact gaatggttca ggaatgacta gtgccataaa atgttggggt tcatttcctg    5700
ggtgtaggcc atttactaac tatttcagtt atgagactaa taggactgtt agtagagata    5760
ataatactgc tactctgtta gatacttatc aaagagaaat aacaaacata tacaggacat    5820
cttgtgtgga tagtgatcac tgtcaagaat ataaatgtaa gcaagtacag ttgaaaaaga    5880
acagcaataa cattataatg aataattgta gtaacaatag gtgtgaagag ttttgggggt    5940
ttagctggtt agaatgtaat cagacagaaa atgcaataac tatattggtc ccagaaatag    6000
aaatacagca agaaagaac acttggattc caaaaggtg tgagaaaact tgggctaagg     6060
taaaacattg tccaatggat ttattatatg gtataaataa aataagaatg tgtgtccaac    6120
ctccattctt tttgtttaaa cagaatgata cttctaataa tactaatatt ctcagtaatt    6180 gtggacctt agtatttctt ggaatatttg aggacaataa ggcagcaatc cagaatggga     6240
gttgcactct tcacaggaca aatattaaca ggccagatta tagtggattt taccaagtgc    6300
ctatatttta tatatgcacc ttgacaggat ttcaaagttg taataatgga tcaataatta    6360
gtataattat gtatgagtct aataatgttc aatacttgtt atgcaatact agtaatacta    6420
atagtaccaa taatgctaat gtctcttgtg tggtacaaag ttttggagtg ataggacagg    6480
cacatgtggc attgcccaga aaaaataaga ggttacaatc tccaaagttt gctcactata    6540
attgcaccat aaataataaa acagagttaa ggcgatggca attggtaaaa acatcaggca    6600
tcactccttt acccatttcc tctacagcta atactggatt agtcagacac aagagagact    6660
ttggtatatc tgctataata gctgccattg tagctgctag tgctattgct gctagtgcta    6720
ctatgtctta tcgcttttg acagaagtca acaaattaga tagtgtacaa aatcatactt     6780
ttgaagtaga gaacaatact atcaataaca tagagttaac agaagagcaa attcatatat    6840
tatatgctat ggttctccaa acacatgcag atgttcaatt gttaaagaa caacaaaaga     6900 ttgaggaaac atttaattta attggatgta tagaaagatc acatcacttt tgtcatactg    6960
gacatccctg gaatgaatca tggggtcagt taaatgattc tacacagtgg gatgactggg    7020
tagataagat ggaaaattta aatcatgata tattaacaac acttcatact gctagaaata    7080
atctagaaca atctatgata actttcaata cacctgacag tgtagcacaa tttggaaaaa    7140
atatttggag tcatattgca aattggattc ctagattagg agcttccata attaaatata    7200
tagtgttgat attacttata tatgtgttac taacctctgc acctaagatc ctcagaggcc    7260
tcttgacaac gatgagtgtt gcaggatcct ccgccagtcg ctacctgaag aaaagatacc    7320
atcacaaaca tgcatcgcga ggagacatct gggcccaggt ccaatatcat gcgtacctgg    7380
cagacgagac tcatggctca ggggacaagt ccaacatgcg gaagctctcc aggaacaact    7440
ggaatggcga atcagaggag tacaacagac gacaaaaaaa ttggaaaaag ttattaaaga    7500
gatctggaga gaattacaat acacacgaag acaacatggg gactatggt cgtttggtga     7560 ctaccgccgc cgagaagaag aacgtcgggg tgaatcctca ccaagggtcc ttaaccctgg    7620
agattcaaag caaaggagga aacatctatg actgttgcat taaggctcaa gaaggaactc    7680
ttgctattcc ttgctgtggc ttcccactat ggccgttttg gggacttata atcatattag    7740
```

```
aacgcttgtt gggatatggg cttcgggaaa ttgcaaaaat tataatgatt ctagggaaag      7800
gactaagtat aataattaca ggattaagaa aattatgtga ttatattggg aaaatgctaa      7860
atccagctac atctcatgta acaatgcctc aatatgatgt ttagaaaaac aagggggggaa      7920 ctgtgggatt aatataagat tcttataagt gaatatgaaa gttgctgatg ctctcaagtt      7980
gctgatgctc tcataacctt atgactagct catgttgcca ggcaactgaa ctgtgataac      8040
cttttgttcc tcattatagt tccgcttttg tatagttccg cttttgtgac gcgttaagtt      8100
cctgttttta cagtatataa gtgcttatat tctgacattt ggtcactcag attctgcggt      8160
ctgagtccct tctctgctgg gctagactag cctttgtaat aaatataatt ctctgctaag      8220
tccctgtctc tagtttgtct tgttttcaag atctaaca                              8258

<210> SEQ ID NO 2
<211> LENGTH: 1461
<212> TYPE: DNA
<213> ORGANISM: Equine Infectious Anemia Virus (EIAV)

<400> SEQUENCE: 2
atgggagact ctttgacatg gagcaaagcg ctcaagaagt tagagaaggt gacggtacaa        60
gggtctcaaa agctaactag tggtaactgt aattgggcgc tgaatttggt ggacttattc       120
catgacacca attttggtaa agaaaaagac tggcaattaa gggacgtcat tccattgtta       180
gaggacgttt cccagacgtt gtcaggacaa gagagagagg catttgaaaa aacttggtgg       240
gcaatagctg ccgttaagat gggcttacaa attaatactg tgaatgatgc aaaaacaaca       300
ttttctatat aaaagccaa gtttgaaaga aagactgcaa ataataccaa aaagcagtct        360
gagcccgagg aagaataccc aataatgatt gatggggctg gaaacagaaa ctttcggcca       420
ttaacaccca gaggatatac tacctgggta aatactatac agcaaaacaa tctcttaaat       480
gaagctagtg tgaatttatt tggtattttta tcagtagact gtacttctga ggaaatgaat      540
gcatttttgg atgtagtacc aggacaagca ggacaaaaac aagtactatt ggataatctt       600
gataagattg cagaagaatg ggatcgtagg cacccgttgc caaatcctcc attagtggca       660
ccaccacaag ggcctattcc catgacagca aggttcatta ggggattggg agttcctaga       720
gaaagacaga tgaaacctgc ttttgatcag tttagacaaa cttatagaca atggataata       780
gaagcaatga cagaagggat aaaaataatg attgggaaac ccaaagcgca aatattagg        840 caaggaccca agaaccccta tccagagttt atagacagat tgctgtctca gataaaaagt       900
gagggacatc cggctgatat aactaaattc ctgacagaca ctttaactat tcagaatgct       960
aatgatgaat gcaaaaatgc tatgagacat ttgaggccag aagatacttt agaagagaaa      1020
atgtatgcat gtagagatat tggcactatg agacaaaaaa tggcattatt agccaaggca      1080
cttcaagcag gattagctgg tcctatgaag ggaggaatat ttaaggggg acccttaggg      1140 gcgaagcaga catgttataa ttgtggaaaa ccaggacatt tttctagtca atgtaaagca      1200
cctaaaatat gttttaagtg caaacagcca ggacatttct caaaacaatg tataaatgct      1260
ccaaaaaacg ggaacaagg ggctcagggg aggccccaga aacaaacttt ccctgtgcag        1320
aaggagtcaa tgaacaaaac acaaaaagag gagaaacagc aagggacctt atatccagat      1380
ttaagtcaga tgaacagga atacaagatc aaggaagagg aaaatcaaga ggatctcaat      1440
ctgaacagtt tgtgggagta a                                                1461

<210> SEQ ID NO 3
<211> LENGTH: 3432
```

<212> TYPE: DNA
<213> ORGANISM: Equine Infectious Anemia Virus (EIAV)

<400> SEQUENCE: 3

```
acagccagga catttctcaa acaatgtat aaatgctcca aaaaacggga aacaaggggc     60
tcagggagg ccccagaaac aaactttccc tgtgcagaag gagtcaatga acaaaacaca    120
aaagaggag aaacagcaag ggaccttata tccagattta agtcagatga acaggaata    180
caagatcaag gaagaggaaa atcaagagga tctcaatctg aacagtttgt gggagtaact    240
tataatttag aaaagagacc aactacaata gtcttgatta tgacacacc cttaaatgta     300
ttgttggaca caggagcaga cacatcagta ctaactattg cacattgtaa taggttaaag    360
tatggaggaa gaaaatatca aggtacaggt attgttgggg ttggaggtaa tgtagaaaca    420
ttttccactc ctgttacagt gaaaagaaa ggaaaacaaa ttaaaactag aatgttagta    480
gcagatatcc cagttactat tttggggcga gatattcttc aagaattagg cgcacaatta    540
ctaatggctc aactttcaaa agaaataacc ccaagagaaa ttaaattaaa aacaggcaca    600
gtagggccta aggttcccca atggccactt actaaagaga agttgttagg tgctaaagaa    660
atagtcaaaa aattgttgga tgaaggtaaa atatcagaag ccagtgatga taatccttat    720
aattctccta tatttgtaat aaaaaagaaa tctggaaagt ggagattatt gcaagattta    780
agagagttaa ttaagggtgg tacaagtaga actgaaatat ccagaggatt acctcatcca    840
gggggattaa ttaaatgtaa tcatatgaca gtattagata ttggagatgc atatttcact    900
ataccattag atccaaagtt tagacaatat acagcattta ctgtgccatc cattaatcat    960
caggaaccag ataaagata tgtgtggaat tgcttgccac aaggttttgt gttaagtcca   1020
tacatatatc aaaaacatt acaggacata ttacaagctt ttagagaaag gcatccagat   1080
gtacaattat atcaatata ggatgattta ttcattggga gtaatgaatc taaaagacaa   1140
cataaggaac tagtagaaga attaagagct attcttttag aaaagggctt tgagacgcct   1200
ggggataaat tgcaggaaga agcaccctat aattggctgg gatatcaact tagtccaggc   1260
aattggaaag tacaaaagat gcaattagaa ttggtaaaag agccaacatt aaatgatgtg   1320
caaaaatcaa agggaaatat aacatggatg agctcagggg ttcctggatt aacagtgaag   1380
caaatagctg ctaccactaa aggttgctta gatttaaatc ataaaggtag taggaccaga   1440
gaagcccaaa aagacttaga ggaaattatt aaaagtttca gaagctcagg attcccatat   1500
tataacccag aagaagaagt aatctgtgag attgaaatta ctaaaaatta tgaggctact   1560
tatataataa aacagtctca aggaatattg tgggcaggaa agaaaattat gagggctaat   1620
aaaggatggt ccgcagcaaa aaatctaatg ttattgttac aacatgtagc cacagaaagt   1680
attgttagaa ttggaacatg tccaaaattt aaagtaccct ttactaaaga acaagtcaaa   1740
tgggaaatgg aaaagggatg gtattattca tggctaccag acatggtata ttcacatcaa   1800
gttgttcatg atgattggag actgaaatta gtagagcaac caacatctgg tataacaatt   1860
tatactgatg ggggtaaaca gaatgaagaa ggagttgcag cttatgtgac tagtaatggg   1920
aaaactaaac aaaaaaggtt agggcctgtt actcatcaaa ctgctgagag gatagcaata   1980
caaatggcat tagaagatac tgaagagaca ttggtaaata tagtaactga tagttactac   2040
tgttggaaaa atattacaga aggattaggg ttagaaggac cagacagccc ctggtggcca   2100
ataattcaaa atattagggc taagaaaatg gtttattttg cttgggtacc aggtcacaaa   2160
ggaatatatg gcaatcaatt ggcagatgag gctactaaaa taacagagga aattatgtta   2220
```

-continued

| | |
|---|---|
| gcatatcaag gcacacagat tagggaaaaa agagatgaag atgcagggta tgatttgtgt | 2280 |
| attccttatg acataatgat acctgtctct gagacaaaag ttatacccac agatgtaaaa | 2340 |
| atacaggtac ctcacaaatg ttttggatgg gtaactggta agtcatcaat ggctaagcaa | 2400 |
| ggattattaa tcaatggggg aataattgat gaaggataca caggtgaaat acaggtaatt | 2460 |
| tgtactaata ttggaaagag taacatgaaa ctcaggaag acaaaagtt tgcacaatta | 2520 |
| atcatattac agcatcgatc aaatgataaa caaatctggg atgaaaataa aacatctcaa | 2580 |
| aggggagata aagggtttgg aagcacaggt atattttggg tagagaatat ccaagaggcg | 2640 |
| caagatgaac atgaaaattg gcatacatct ccaaagatat tggcaaaaag atatgggtta | 2700 |
| ccattgactg tagctaaaca gataactcaa gaatgccctc attgtactaa acaaggatct | 2760 |
| ggaccagcag gttgtgtaat gagatctcct aatcattggc aggctgattg tacacattta | 2820 |
| gaaaacaggg taataatgac atttgtagag tctaattcag gatacattca tgctactcta | 2880 |
| ttgtccaaag aaaatgcctt gtgtccttca ttggctattt tggaatgggt gaggttattt | 2940 |
| tctcctaaat ctttacatac agacaatggt actaattttg tggcagagtc agtagcaaat | 3000 |
| ctgttgaaat tcctgaaggt gacacatact acaggaatac cttatcaccc agagagccaa | 3060 |
| ggcattgtgg aaagagcaaa caggacatta aaagaaagaa ttaaaagtca tagaggaaat | 3120 |
| actcagacac ttgaagcagc attacaactt gctctcatta cttgtaacaa agggagggaa | 3180 |
| agtatgggag acaaactcc atgggaagta tttattacta atcaggctca aacaatacat | 3240 |
| gaagaacttt tattcaaca agcacaatct tctaaaaaat tttgttttta taaaattcct | 3300 |
| ggtgagcata attggaaggg gcccaccaga gtgttgtgga aaggtgatgg agcagtagtg | 3360 |
| gtcaatgatg aggaaaaagg aataattgct gtgcctttaa ccaggactaa attattaata | 3420 |
| agaccaaatt ga | 3432 |

<210> SEQ ID NO 4
<211> LENGTH: 2592
<212> TYPE: DNA
<213> ORGANISM: Equine Infectious Anemia Virus (EIAV)

<400> SEQUENCE: 4

| | |
|---|---|
| atggtcagca ttacattcta tgggggtatc ccagggggaa tatcaacccc tatcacccaa | 60 |
| caaacagaat caacagacac acagaaaggg gatcatatgg tatatcaacc ctattgttat | 120 |
| aatgatagcc ataaagaaga aatggcagag acaagagaca caagatacca agaagaaatg | 180 |
| aaccggaaag aagataaaga agataaaaga aagaataact ggtggaagat aggtatgttc | 240 |
| ttattgtgtc tgttagagat cactggagga ttcctctggt ggtatgagag gcaacaacat | 300 |
| tcatattata taagattggt tacaatagga ggtagactga atggttcagg aatgactagt | 360 |
| gccataaaat gttggggttc atttcctggg tgtaggccat ttactaacta tttcagttat | 420 |
| gagactaata ggactgttag tagagataat aatactgcta ctctgttaga tacttatcaa | 480 |
| agagaaataa caaacatata caggacatct tgtgtggata tgatcactg tcaagaatat | 540 |
| aaatgtaagc aagtacagtt gaaaagaac agcaataaca ttataatgaa taattgtagt | 600 |
| aacaataggt gtgaagagtt ttgggggttt agctggttag aatgtaatca gacagaaaat | 660 |
| gcaataacta tattggtccc agaaatagaa atacagcaaa gaagaacac ttggattcca | 720 |
| aaaaggtgtg agaaaacttg ggctaaggta aacattgtc caatggattt attatatggt | 780 |
| ataaataaaa taagaatgtg tgtccaacct ccattctttt tgtttaaaca gaatgatact | 840 |
| tctaataata ctaatattct cagtaattgt ggacctttag tatttcttgg aatatttgag | 900 |

-continued

| | |
|---|---|
| gacaataagg cagcaatcca gaatgggagt tgcactcttc acaggacaaa tattaacagg | 960 |
| ccagattata gtggatttta ccaagtgcct atattttata tatgcacctt gacaggattt | 1020 |
| caaagttgta ataatggatc aataattagt ataattatgt atgagtctaa taatgttcaa | 1080 |
| tacttgttat gcaatactag taatactaat agtaccaata atgctaatgt ctcttgtgtg | 1140 |
| gtacaaagtt ttggagtgat aggacaggca catgtggcat tgcccagaaa aaataagagg | 1200 |
| ttacaatctc caagtttgc tcactataat tgcaccataa ataataaaac agagttaagg | 1260 |
| cgatggcaat tggtaaaaac atcaggcatc actcctttac ccatttcctc tacagctaat | 1320 |
| actggattag tcagacacaa gagagacttt ggtatatctg ctataatagc tgccattgta | 1380 |
| gctgctagtg ctattgctgc tagtgctact atgtcttata tcgctttgac agaagtcaac | 1440 |
| aaattagata gtgtacaaaa tcatactttt gaagtagaga acaatactat caataacata | 1500 |
| gagttaacag aagagcaaat tcatatatta tatgctatgg ttctccaaac acatgcagat | 1560 |
| gttcaattgt taaaagaaca acaaaagatt gaggaaacat ttaatttaat tggatgtata | 1620 |
| gaaagatcac atacattttg tcatactgga catccctgga atgaatcatg gggtcagtta | 1680 |
| aatgattcta cacagtggga tgactgggta gataagatgg aaaatttaaa tcatgatata | 1740 |
| ttaacaacac ttcatactgc tagaaataat ctagaacaat ctatgataac tttcaataca | 1800 |
| cctgacagtg tagcacaatt tggaaaaaat atttggagtc atattgcaaa ttggattcct | 1860 |
| agattaggag cttccataat taaatatata gtgttgatat tacttatata tgtgttacta | 1920 |
| acctctgcac taagatcct cagaggcctc ttgacaacga tgagtggtgc aggatcctcc | 1980 |
| gccagtcgct acctgaagaa aagataccat cacaaacatg catcgcgagg agacatctgg | 2040 |
| gcccaggtcc aatatcatgc gtacctggca gacgagactc atggctcagg ggacaagtcc | 2100 |
| aacatgcgga agctctccag gaacaactgg aatggcgaat cagaggagta caacagacga | 2160 |
| caaaaaatt ggaaaaagtt attaaagaga tctggagaga attacaatac acacgaagac | 2220 |
| aacatgggga ctatgggtcg tttggtgact accgccgccg agaagaagaa cgtcggggtg | 2280 |
| aatcctcacc aagggtcctt aaccctggag attcaaagca aggaggaaa catctatgac | 2340 |
| tgttgcatta aggctcaaga aggaactctt gctattcctt gctgtggctt cccactatgg | 2400 |
| ccgtttggg gacttataat catattagaa cgcttgttgg gatatgggct tcgggaaatt | 2460 |
| gcaaaaatta taatgattct agggaaagga ctaagtataa taattacagg attaagaaaa | 2520 |
| ttatgtgatt atattgggaa aatgctaaat ccagctacat ctcatgtaac aatgcctcaa | 2580 |
| tatgatgttt ag | 2592 |

<210> SEQ ID NO 5
<211> LENGTH: 495
<212> TYPE: DNA
<213> ORGANISM: Equine Infectious Anemia Virus (EIAV)

<400> SEQUENCE: 5

| | |
|---|---|
| atggcagaga caagagacac aagataccaa gaagaaatga accggaaaga agataaagaa | 60 |
| gataaaagaa agaataactg gtggaagata ggtcctcaga ggcctcttga caacgatgag | 120 |
| tggtgcagga tcctccgcca gtcgctacct gaagaaaaga taccatcaca acatgcatc | 180 |
| gcgaggagac atctgggccc aggtccaata tcatgcgtac ctggcagacg agactcatgg | 240 |
| ctcaggggac aagtccaaca tgcggaagct ctccaggaac aactggaatg gcgaatcaga | 300 |
| ggagtacaac agacgacaaa aaaattggaa aaagttatta agagatctg gagagaatta | 360 |

```
caatacacac gaagacaaca tggggactat gggtcgtttg gtgactaccg ccgccgagaa      420
gaagaacgtc ggggtgaatc ctcaccaagg gtccttaacc ctggagattc aaagcaaagg      480
aggaaacatc tatga                                                      495

<210> SEQ ID NO 6
<211> LENGTH: 237
<212> TYPE: DNA
<213> ORGANISM: Equine Infectious Anemia Virus (EIAV)

<400> SEQUENCE: 6
ctgctgaacc tggctgatca taggatccct aggacagcag aggagaactt acagaagtct       60
tctggaggtg ttcctggcca acacagga agacaggtac caccagtcag ctatcattgt       120
caactgtgtt tcctgagatc attgggaatt gactaccttg acagctcgct gaagaagaag      180
aacaaacaaa gacagaaggc catcagggag gaagacaacc tcagtatctt gttataa        237

<210> SEQ ID NO 7
<211> LENGTH: 207
<212> TYPE: DNA
<213> ORGANISM: Equine Infectious Anemia Virus (EIAV)

<400> SEQUENCE: 7
atgggattat ttggtaaagg ggtaacatgg tcagcattac attctatggg ggtatcccag       60
ggggaatatc aaccctatc acccaacaaa cagaatcaac agacacacag aaagggatc       120 atatggtata tcaaccctat tgttataatg atagccataa agaagaaatg gcagagacaa      180
gagacacaag ataccaagaa gaaatga                                         207

<210> SEQ ID NO 8
<211> LENGTH: 486
<212> TYPE: PRT
<213> ORGANISM: Equine Infectious Anemia Virus (EIAV)

<400> SEQUENCE: 8

Met Gly Asp Ser Leu Thr Trp Ser Lys Ala Leu Lys Lys Leu Glu Lys
1               5                   10                  15

Val Thr Val Gln Gly Ser Gln Lys Leu Thr Ser Gly Asn Cys Asn Trp
            20                  25                  30

Ala Leu Asn Leu Val Asp Leu Phe His Asp Thr Asn Phe Gly Lys Glu
        35                  40                  45

Lys Asp Trp Gln Leu Arg Asp Val Ile Pro Leu Leu Glu Asp Val Ser
    50                  55                  60

Gln Thr Leu Ser Gly Gln Glu Arg Glu Ala Phe Glu Lys Thr Trp Trp
65                  70                  75                  80

Ala Ile Ala Ala Val Lys Met Gly Leu Gln Ile Asn Thr Val Asn Asp
                85                  90                  95

Ala Lys Thr Thr Phe Ser Ile Leu Lys Ala Lys Phe Glu Arg Lys Thr
            100                 105                 110

Ala Asn Asn Thr Lys Lys Gln Ser Glu Pro Glu Glu Glu Tyr Pro Ile
        115                 120                 125

Met Ile Asp Gly Ala Gly Asn Arg Asn Phe Arg Pro Leu Thr Pro Arg
    130                 135                 140

Gly Tyr Thr Thr Trp Val Asn Thr Ile Gln Gln Asn Asn Leu Leu Asn
145                 150                 155                 160

Glu Ala Ser Val Asn Leu Phe Gly Ile Leu Ser Val Asp Cys Thr Ser
                165                 170                 175
```

```
Glu Glu Met Asn Ala Phe Leu Asp Val Val Pro Gly Gln Ala Gly Gln
            180                 185                 190

Lys Gln Val Leu Leu Asp Asn Leu Asp Lys Ile Ala Glu Glu Trp Asp
        195                 200                 205

Arg Arg His Pro Leu Pro Asn Pro Pro Leu Val Ala Pro Pro Gln Gly
    210                 215                 220

Pro Ile Pro Met Thr Ala Arg Phe Ile Arg Gly Leu Gly Val Pro Arg
225                 230                 235                 240

Glu Arg Gln Met Lys Pro Ala Phe Asp Gln Phe Arg Gln Thr Tyr Arg
                245                 250                 255

Gln Trp Ile Ile Glu Ala Met Thr Glu Gly Ile Lys Ile Met Ile Gly
            260                 265                 270

Lys Pro Lys Ala Gln Asn Ile Arg Gln Gly Pro Lys Glu Pro Tyr Pro
        275                 280                 285

Glu Phe Ile Asp Arg Leu Leu Ser Gln Ile Lys Ser Glu Gly His Pro
    290                 295                 300

Ala Asp Ile Thr Lys Phe Leu Thr Asp Thr Leu Thr Ile Gln Asn Ala
305                 310                 315                 320

Asn Asp Glu Cys Lys Asn Ala Met Arg His Leu Arg Pro Glu Asp Thr
                325                 330                 335

Leu Glu Glu Lys Met Tyr Ala Cys Arg Asp Ile Gly Thr Met Arg Gln
            340                 345                 350

Lys Met Ala Leu Leu Ala Lys Ala Leu Gln Ala Gly Leu Ala Gly Pro
        355                 360                 365

Met Lys Gly Gly Ile Phe Lys Gly Gly Pro Leu Gly Ala Lys Gln Thr
    370                 375                 380

Cys Tyr Asn Cys Gly Lys Pro Gly His Phe Ser Ser Gln Cys Lys Ala
385                 390                 395                 400

Pro Lys Ile Cys Phe Lys Cys Lys Gln Pro Gly His Phe Ser Lys Gln
                405                 410                 415

Cys Arg Asn Ala Pro Lys Asn Gly Lys Gln Gly Ala Gln Gly Arg Pro
            420                 425                 430

Gln Lys Gln Thr Phe Pro Val Gln Lys Glu Ser Met Asn Lys Thr Gln
        435                 440                 445

Lys Glu Glu Lys Gln Gln Gly Thr Leu Tyr Pro Asp Leu Ser Gln Met
    450                 455                 460

Lys Gln Glu Tyr Lys Ile Lys Glu Glu Glu Asn Gln Glu Asp Leu Asn
465                 470                 475                 480

Leu Asn Ser Leu Trp Glu
                485

<210> SEQ ID NO 9
<211> LENGTH: 1143
<212> TYPE: PRT
<213> ORGANISM: Equine Infectious Anemia Virus (EIAV)

<400> SEQUENCE: 9

Thr Ala Arg Thr Phe Leu Lys Thr Met Tyr Lys Cys Ser Lys Lys Arg
1               5                   10                  15

Glu Thr Arg Gly Ser Gly Glu Ala Pro Glu Thr Asn Phe Pro Cys Ala
            20                  25                  30

Glu Gly Val Asn Glu Gln Asn Thr Lys Arg Gly Glu Thr Ala Arg Asp
        35                  40                  45

Leu Ile Ser Arg Phe Lys Ser Asp Glu Thr Gly Ile Gln Asp Gln Gly
    50                  55                  60
```

```
Arg Gly Lys Ser Arg Gly Ser Gln Ser Glu Gln Phe Val Gly Val Thr
 65                  70                  75                  80

Tyr Asn Leu Glu Lys Arg Pro Thr Thr Ile Val Leu Ile Asn Asp Thr
                 85                  90                  95

Pro Leu Asn Val Leu Leu Asp Thr Gly Ala Asp Thr Ser Val Leu Thr
                100                 105                 110

Ile Ala His Cys Asn Arg Leu Lys Tyr Gly Gly Arg Lys Tyr Gln Gly
            115                 120                 125

Thr Gly Ile Val Gly Val Gly Gly Asn Val Glu Thr Phe Ser Thr Pro
        130                 135                 140

Val Thr Val Lys Lys Lys Gly Lys Gln Ile Lys Thr Arg Met Leu Val
145                 150                 155                 160

Ala Asp Ile Pro Val Thr Ile Leu Gly Arg Asp Ile Leu Gln Glu Leu
                165                 170                 175

Gly Ala Gln Leu Leu Met Ala Gln Leu Ser Lys Glu Ile Thr Pro Arg
            180                 185                 190

Glu Ile Lys Leu Lys Thr Gly Thr Val Gly Pro Lys Val Pro Gln Trp
        195                 200                 205

Pro Leu Thr Lys Glu Lys Leu Leu Gly Ala Lys Glu Ile Val Lys Lys
210                 215                 220

Leu Leu Asp Glu Gly Lys Ile Ser Glu Ala Ser Asp Asp Asn Pro Tyr
225                 230                 235                 240

Asn Ser Pro Ile Phe Val Ile Lys Lys Lys Ser Gly Lys Trp Arg Leu
                245                 250                 255

Leu Gln Asp Leu Arg Glu Leu Ile Lys Gly Gly Thr Ser Arg Thr Glu
            260                 265                 270

Ile Ser Arg Gly Leu Pro His Pro Gly Gly Leu Ile Lys Cys Asn His
        275                 280                 285

Met Thr Val Leu Asp Ile Gly Asp Ala Tyr Phe Thr Ile Pro Leu Asp
    290                 295                 300

Pro Lys Phe Arg Gln Tyr Thr Ala Phe Thr Val Pro Ser Ile Asn His
305                 310                 315                 320

Gln Glu Pro Asp Lys Arg Tyr Val Trp Asn Cys Leu Pro Gln Gly Phe
                325                 330                 335

Val Leu Ser Pro Tyr Ile Tyr Gln Lys Thr Leu Gln Asp Ile Leu Gln
            340                 345                 350

Ala Phe Arg Glu Arg His Pro Asp Val Gln Leu Tyr Gln Tyr Met Asp
        355                 360                 365

Asp Leu Phe Ile Gly Ser Asn Glu Ser Lys Arg Gln His Lys Glu Leu
    370                 375                 380

Val Glu Glu Leu Arg Ala Ile Leu Leu Glu Lys Gly Phe Glu Thr Pro
385                 390                 395                 400

Gly Asp Lys Leu Gln Glu Glu Ala Pro Tyr Asn Trp Leu Gly Tyr Gln
                405                 410                 415

Leu Ser Pro Gly Asn Trp Lys Val Gln Lys Met Gln Leu Glu Leu Val
            420                 425                 430

Lys Glu Pro Thr Leu Asn Asp Val Gln Lys Ser Lys Gly Asn Ile Thr
        435                 440                 445

Trp Met Ser Ser Gly Val Pro Gly Leu Thr Val Lys Gln Ile Ala Ala
    450                 455                 460

Thr Thr Lys Gly Cys Leu Asp Leu Asn His Lys Gly Ser Arg Thr Arg
465                 470                 475                 480
```

-continued

```
Glu Ala Gln Lys Asp Leu Glu Ile Ile Lys Ser Phe Arg Ser Ser
            485                 490                 495
Gly Phe Pro Tyr Tyr Asn Pro Glu Glu Val Ile Cys Glu Ile Glu
            500                 505                 510
Ile Thr Lys Asn Tyr Glu Ala Thr Tyr Ile Ile Lys Gln Ser Gln Gly
            515                 520                 525
Ile Leu Trp Ala Gly Lys Lys Ile Met Arg Ala Asn Lys Gly Trp Ser
            530                 535                 540
Ala Ala Lys Asn Leu Met Leu Leu Gln His Val Ala Thr Glu Ser
545             550                 555                 560
Ile Val Arg Ile Gly Thr Cys Pro Lys Phe Lys Val Pro Phe Thr Lys
                565                 570                 575
Glu Gln Val Lys Trp Glu Met Glu Lys Gly Trp Tyr Tyr Ser Trp Leu
            580                 585                 590
Pro Asp Met Val Tyr Ser His Gln Val Val His Asp Asp Trp Arg Leu
            595                 600                 605
Lys Leu Val Glu Gln Pro Thr Ser Gly Ile Thr Ile Tyr Thr Asp Gly
            610                 615                 620
Gly Lys Gln Asn Glu Glu Gly Val Ala Ala Tyr Val Thr Ser Asn Gly
625                 630                 635                 640
Lys Thr Lys Gln Lys Arg Leu Gly Pro Val Thr His Gln Thr Ala Glu
                645                 650                 655
Arg Ile Ala Ile Gln Met Ala Leu Glu Asp Thr Glu Thr Leu Val
            660                 665                 670
Asn Ile Val Thr Asp Ser Tyr Tyr Cys Trp Lys Asn Ile Thr Glu Gly
                675                 680                 685
Leu Gly Leu Glu Gly Pro Asp Ser Pro Trp Trp Pro Ile Ile Gln Asn
            690                 695                 700
Ile Arg Ala Lys Glu Met Val Tyr Phe Ala Trp Val Pro Gly His Lys
705                 710                 715                 720
Gly Ile Tyr Gly Asn Gln Leu Ala Asp Glu Ala Thr Lys Ile Thr Glu
                725                 730                 735
Glu Ile Met Leu Ala Tyr Gln Gly Thr Gln Ile Arg Glu Lys Arg Asp
            740                 745                 750
Glu Asp Ala Gly Tyr Asp Leu Cys Ile Pro Tyr Asp Ile Met Ile Pro
            755                 760                 765
Val Ser Glu Thr Lys Val Ile Pro Thr Asp Val Lys Ile Gln Val Pro
770                 775                 780
His Lys Cys Phe Gly Trp Val Thr Gly Lys Ser Ser Met Ala Lys Gln
785                 790                 795                 800
Gly Leu Leu Ile Asn Gly Gly Ile Ile Asp Glu Gly Tyr Thr Gly Glu
                805                 810                 815
Ile Gln Val Ile Cys Thr Asn Ile Gly Lys Ser Asn Met Lys Leu Arg
            820                 825                 830
Glu Gly Gln Lys Phe Ala Gln Leu Ile Ile Leu Gln His Arg Ser Asn
            835                 840                 845
Asp Lys Gln Ile Trp Asp Glu Asn Lys Thr Ser Gln Arg Gly Asp Lys
            850                 855                 860
Gly Phe Gly Ser Thr Gly Ile Phe Trp Val Glu Asn Ile Gln Glu Ala
865                 870                 875                 880
Gln Asp Glu His Glu Asn Trp His Thr Ser Pro Lys Ile Leu Ala Lys
                885                 890                 895
Arg Tyr Gly Leu Pro Leu Thr Val Ala Lys Gln Ile Thr Gln Glu Cys
```

-continued

```
            900                 905                 910

Pro His Cys Thr Lys Gln Gly Ser Gly Pro Ala Gly Cys Val Met Arg
        915                 920                 925

Ser Pro Asn His Trp Gln Ala Asp Cys Thr His Leu Glu Asn Arg Val
    930                 935                 940

Ile Met Thr Phe Val Glu Ser Asn Ser Gly Tyr Ile His Ala Thr Leu
945                 950                 955                 960

Leu Ser Lys Glu Asn Ala Leu Cys Pro Ser Leu Ala Ile Leu Glu Trp
                965                 970                 975

Val Arg Leu Phe Ser Pro Lys Ser Leu His Thr Asp Asn Gly Thr Asn
            980                 985                 990

Phe Val Ala Glu Ser Val Ala Asn  Leu Leu Lys Phe Leu  Lys Val Thr
        995                 1000                1005

His Thr  Thr Gly Ile Pro Tyr  His Pro Glu Ser Gln  Gly Ile Val
    1010                1015                1020

Glu Arg  Ala Asn Arg Thr Leu  Lys Glu Arg Ile Lys  Ser His Arg
    1025                1030                1035

Gly Asn  Thr Gln Thr Leu Glu  Ala Ala Leu Gln Leu  Ala Leu Ile
    1040                1045                1050

Thr Cys  Asn Lys Gly Arg Glu  Ser Met Gly Gly Gln  Thr Pro Trp
    1055                1060                1065

Glu Val  Phe Ile Thr Asn Gln  Ala Gln Thr Ile His  Glu Glu Leu
    1070                1075                1080

Leu Leu  Gln Gln Ala Gln Ser  Ser Lys Lys Phe Cys  Phe Tyr Lys
    1085                1090                1095

Ile Pro  Gly Glu His Asn Trp  Lys Gly Pro Thr Arg  Val Leu Trp
    1100                1105                1110

Lys Gly  Asp Gly Ala Val Val  Val Asn Asp Glu Glu  Lys Gly Ile
    1115                1120                1125

Ile Ala  Val Pro Leu Thr Arg  Thr Lys Leu Leu Ile  Arg Pro Asn
    1130                1135                1140

<210> SEQ ID NO 10
<211> LENGTH: 863
<212> TYPE: PRT
<213> ORGANISM: Equine Infectious Anemia Virus (EIAV)

<400> SEQUENCE: 10

Met Val Ser Ile Thr Phe Tyr Gly Gly Ile Pro Gly Gly Ile Ser Thr
1               5                   10                  15

Pro Ile Thr Gln Gln Thr Glu Ser Thr Asp Thr Gln Lys Gly Asp His
            20                  25                  30

Met Val Tyr Gln Pro Tyr Cys Tyr Asn Asp Ser His Lys Glu Glu Met
        35                  40                  45

Ala Glu Thr Arg Asp Thr Arg Tyr Gln Glu Glu Met Asn Arg Lys Glu
    50                  55                  60

Asp Lys Glu Asp Lys Arg Lys Asn Asn Trp Trp Lys Ile Gly Met Phe
65                  70                  75                  80

Leu Leu Cys Leu Leu Glu Ile Thr Gly Gly Phe Leu Trp Trp Tyr Glu
                85                  90                  95

Arg Gln Gln His Ser Tyr Tyr Ile Arg Leu Val Thr Ile Gly Gly Arg
            100                 105                 110

Leu Asn Gly Ser Gly Met Thr Ser Ala Ile Lys Cys Trp Gly Ser Phe
        115                 120                 125
```

```
Pro Gly Cys Arg Pro Phe Thr Asn Tyr Phe Ser Tyr Glu Thr Asn Arg
    130                 135                 140

Thr Val Ser Arg Asp Asn Asn Thr Ala Thr Leu Leu Asp Thr Tyr Gln
145                 150                 155                 160

Arg Glu Ile Thr Asn Ile Tyr Arg Thr Ser Cys Val Asp Ser Asp His
                165                 170                 175

Cys Gln Glu Tyr Lys Cys Lys Gln Val Gln Leu Lys Lys Asn Ser Asn
            180                 185                 190

Asn Ile Ile Met Asn Asn Cys Ser Asn Asn Arg Cys Glu Glu Phe Trp
        195                 200                 205

Gly Phe Ser Trp Leu Glu Cys Asn Gln Thr Glu Asn Ala Ile Thr Ile
    210                 215                 220

Leu Val Pro Glu Ile Glu Ile Gln Gln Arg Lys Asn Thr Trp Ile Pro
225                 230                 235                 240

Lys Arg Cys Glu Lys Thr Trp Ala Lys Val Lys His Cys Pro Met Asp
                245                 250                 255

Leu Leu Tyr Gly Ile Asn Lys Ile Arg Met Cys Val Gln Pro Pro Phe
            260                 265                 270

Phe Leu Phe Lys Gln Asn Asp Thr Ser Asn Asn Thr Asn Ile Leu Ser
        275                 280                 285

Asn Cys Gly Pro Leu Val Phe Leu Gly Ile Phe Glu Asp Asn Lys Ala
    290                 295                 300

Ala Ile Gln Asn Gly Ser Cys Thr Leu His Arg Thr Asn Ile Asn Arg
305                 310                 315                 320

Pro Asp Tyr Ser Gly Phe Tyr Gln Val Pro Ile Phe Tyr Ile Cys Thr
                325                 330                 335

Leu Thr Gly Phe Gln Ser Cys Asn Asn Gly Ser Ile Ile Ser Ile Ile
            340                 345                 350

Met Tyr Glu Ser Asn Asn Val Gln Tyr Leu Leu Cys Asn Thr Ser Asn
        355                 360                 365

Thr Asn Ser Thr Asn Asn Ala Asn Val Ser Cys Val Val Gln Ser Phe
370                 375                 380

Gly Val Ile Gly Gln Ala His Val Ala Leu Pro Arg Lys Asn Lys Arg
385                 390                 395                 400

Leu Gln Ser Pro Lys Phe Ala His Tyr Asn Cys Thr Ile Asn Asn Lys
                405                 410                 415

Thr Glu Leu Arg Arg Trp Gln Leu Val Lys Thr Ser Gly Ile Thr Pro
            420                 425                 430

Leu Pro Ile Ser Ser Thr Ala Asn Thr Gly Leu Val Arg His Lys Arg
        435                 440                 445

Asp Phe Gly Ile Ser Ala Ile Ala Ala Ile Val Ala Ala Ser Ala
    450                 455                 460

Ile Ala Ala Ser Ala Thr Met Ser Tyr Ile Ala Leu Thr Glu Val Asn
465                 470                 475                 480

Lys Leu Asp Ser Val Gln Asn His Thr Phe Glu Val Glu Asn Asn Thr
                485                 490                 495

Ile Asn Asn Ile Glu Leu Thr Glu Glu Ile His Ile Leu Tyr Ala
            500                 505                 510

Met Val Leu Gln Thr His Ala Asp Val Gln Leu Leu Lys Glu Gln Gln
        515                 520                 525

Lys Ile Glu Glu Thr Phe Asn Leu Ile Gly Cys Ile Glu Arg Ser His
530                 535                 540

Thr Phe Cys His Thr Gly His Pro Trp Asn Glu Ser Trp Gly Gln Leu
```

-continued

Asn Asp Ser Thr Gln Trp Asp Trp Val Asp Lys Met Glu Asn Leu
545                 550                 555                 560

Asn His Asp Ile Leu Thr Thr Leu His Thr Ala Arg Asn Asn Leu Glu
            565                 570                 575

Gln Ser Met Ile Thr Phe Asn Thr Pro Asp Ser Val Ala Gln Phe Gly
        580                 585                 590

Lys Asn Ile Trp Ser His Ile Ala Asn Trp Ile Pro Arg Leu Gly Ala
    595                 600                 605

Ser Ile Ile Lys Tyr Ile Val Leu Ile Leu Ile Tyr Val Leu Leu
610                 615                 620

Thr Ser Ala Pro Lys Ile Leu Arg Gly Leu Leu Thr Thr Met Ser Gly
625                 630                 635                 640

Ala Gly Ser Ser Ala Ser Arg Tyr Leu Lys Lys Arg Tyr His His Lys
        645                 650                 655

His Ala Ser Arg Gly Asp Ile Trp Ala Gln Val Gln Tyr His Ala Tyr
    660                 665                 670

Leu Ala Asp Glu Thr His Gly Ser Gly Asp Lys Ser Asn Met Arg Lys
675                 680                 685

Leu Ser Arg Asn Asn Trp Asn Gly Glu Ser Glu Tyr Asn Arg Arg
690                 695                 700

Gln Lys Asn Trp Lys Lys Leu Leu Lys Arg Ser Gly Glu Asn Tyr Asn
705                 710                 715                 720

Thr His Glu Asp Asn Met Gly Thr Met Gly Arg Leu Val Thr Thr Ala
            725                 730                 735

Ala Glu Lys Lys Asn Val Gly Val Asn Pro His Gln Gly Ser Leu Thr
        740                 745                 750

Leu Glu Ile Gln Ser Lys Gly Gly Asn Ile Tyr Asp Cys Cys Ile Lys
    755                 760                 765

Ala Gln Glu Gly Thr Leu Ala Ile Pro Cys Cys Gly Phe Pro Leu Trp
770                 775                 780

Pro Phe Trp Gly Leu Ile Ile Ile Leu Glu Arg Leu Leu Gly Tyr Gly
785                 790                 795                 800

Leu Arg Glu Ile Ala Lys Ile Ile Met Ile Leu Gly Lys Gly Leu Ser
            805                 810                 815

Ile Ile Ile Thr Gly Leu Arg Lys Leu Cys Asp Tyr Ile Gly Lys Met
        820                 825                 830

Leu Asn Pro Ala Thr Ser His Val Thr Met Pro Gln Tyr Asp Val
    835                 840                 845

850                 855                 860

<210> SEQ ID NO 11
<211> LENGTH: 164
<212> TYPE: PRT
<213> ORGANISM: Equine Infectious Anemia Virus (EIAV)

<400> SEQUENCE: 11

Met Ala Glu Thr Arg Asp Thr Arg Tyr Gln Glu Glu Met Asn Arg Lys
1               5                   10                  15

Glu Asp Lys Glu Asp Lys Arg Lys Asn Asn Trp Trp Lys Ile Gly Pro
            20                  25                  30

Gln Arg Pro Leu Asp Asn Asp Glu Trp Cys Arg Ile Leu Arg Gln Ser
        35                  40                  45

Leu Pro Glu Glu Lys Ile Pro Ser Gln Thr Cys Ile Ala Arg Arg His
    50                  55                  60

```
Leu Gly Pro Gly Pro Ile Ser Cys Val Pro Gly Arg Arg Asp Ser Trp
 65                  70                  75                  80

Leu Arg Gly Gln Val Gln His Ala Glu Ala Leu Gln Glu Gln Leu Glu
                 85                  90                  95

Trp Arg Ile Arg Gly Val Gln Gln Thr Thr Lys Lys Leu Glu Lys Val
            100                 105                 110

Ile Lys Glu Ile Trp Arg Glu Leu Gln Tyr Thr Arg Arg Gln His Gly
        115                 120                 125

Asp Tyr Gly Ser Phe Gly Asp Tyr Arg Arg Glu Glu Glu Arg Arg
    130                 135                 140

Gly Glu Ser Ser Pro Arg Val Leu Asn Pro Gly Asp Ser Lys Gln Arg
145                 150                 155                 160

Arg Lys His Leu

<210> SEQ ID NO 12
<211> LENGTH: 78
<212> TYPE: PRT
<213> ORGANISM: Equine Infectious Anemia Virus (EIAV)

<400> SEQUENCE: 12

Leu Leu Asn Leu Ala Asp His Arg Ile Pro Arg Thr Ala Glu Glu Asn
 1               5                  10                  15

Leu Gln Lys Ser Ser Gly Gly Val Pro Gly His Asn Thr Gly Arg Gln
                20                  25                  30

Val Pro Pro Val Ser Tyr His Cys Gln Leu Cys Phe Leu Arg Ser Leu
            35                  40                  45

Gly Ile Asp Tyr Leu Asp Ser Ser Leu Lys Lys Lys Asn Lys Gln Arg
        50                  55                  60

Gln Lys Ala Ile Arg Glu Asp Asn Leu Ser Ile Leu Leu
 65                  70                  75

<210> SEQ ID NO 13
<211> LENGTH: 68
<212> TYPE: PRT
<213> ORGANISM: Equine Infectious Anemia Virus (EIAV)

<400> SEQUENCE: 13

Met Gly Leu Phe Gly Lys Gly Val Thr Trp Ser Ala Leu His Ser Met
 1               5                  10                  15

Gly Val Ser Gln Gly Glu Tyr Gln Pro Leu Ser Pro Asn Lys Gln Asn
                20                  25                  30

Gln Gln Thr His Arg Lys Gly Ile Ile Trp Tyr Ile Asn Pro Ile Val
            35                  40                  45

Ile Met Ile Ala Ile Lys Lys Lys Trp Gln Arg Gln Glu Thr Gln Asp
        50                  55                  60

Thr Lys Lys Lys
 65

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
gcgcgcgaat tctgtggggt ttttatgag                                    29
```

```
<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aaccttgctg ctatgggaat                                          20

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16 cccctctag atctaggatc tggaacagac                                30

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
accgcaataa ccgcatttgt gacg                                     24

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtaagatggg agacccttg                                           20

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
atgctgacca tgttacccct t                                        21

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
cagatactga ggttgtcttc ct                                       22

<210> SEQ ID NO 21
<211> LENGTH: 22
<212> TYPE: DNA
<213> ORGANISM: Artificial Sequence
<220> FEATURE:
<223> OTHER INFORMATION: primer
```

<400> SEQUENCE: 21
taatcgactc actataggga ga                                    22

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
catacgattt aggtgacact atag                                  24

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
cctcgaggga gatgcatatt tc                                    22

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
ccctcatctc atccatgtt                                        19

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
ggtatagtga aatatgcatc tcc                                   23

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
aagtgaggga catccggct                                        19

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
ctgtcctccc atactttc                                         18

<210> SEQ ID NO 28
<211> LENGTH: 21

<212> TYPE: DNA
<213> ORGANISM: Artificial Sequence
<220> FEATURE:
<223> OTHER INFORMATION: primer

<400> SEQUENCE: 28
ccaacaagga aggacaacct c                                              21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
agacatagta gcgctagcag                                                20

<210> SEQ ID NO 30
<211> LENGTH: 17
<212> TYPE: DNA
<213> ORGANISM: Artificial Sequence
<220> FEATURE:
<223> OTHER INFORMATION: primer

<400> SEQUENCE: 30
gccttaatgc aacagtc                                                   17

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gctactgcta ttgctgctag                                                20

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ctcagaccgc agaatctgag t                                              21

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ggacatccgg ctgatataac                                                20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34

-continued

```
gaccagctaa tcctgcttga                                                    20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gcttgaagtg ccttggctaa                                                    20

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
tcaggaatca ccaccagtca g                                                  21

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gttgttgcct ctcataccac                                                    20

<210> SEQ ID NO 38
<211> LENGTH: 17
<212> TYPE: DNA
<213> ORGANISM: Artificial Sequence
<220> FEATURE:
<223> OTHER INFORMATION: primer

<400> SEQUENCE: 38
agacagattg ctgtctc                                                       17

<210> SEQ ID NO 39
<211> LENGTH: 16
<212> TYPE: DNA
<213> ORGANISM: Artificial Sequence
<220> FEATURE:
<223> OTHER INFORMATION: primer

<400> SEQUENCE: 39
cataggacca gctatc                                                        16
```

FULL-GENE SEQUENCE OF THE DONKEY LEUKOCYTE VACCINE STRAIN OF THE EQUINE INFECTIOUS ANEMIA VIRUS AND THEIR APPLICATION

This is a national stage application under 35 U.S.C. 371 of PCT/CN00/00096, filed on Apr. 21, 2000 designating the U.S., now abandoned.

FIELD OF INVENTION

This invention relates to the full-length genome sequence of the donkey leukocyte attenuated EIAV vaccine strain, as well as the sequences and potential uses of the functional genes and their expression products.

BACKGROUND

Equine Infectious Anemia Virus (EIAV), the pathogen of Equine Infectious Anemia, was the first kind of virus discovered by human. Equine Infectious Anemia, first described in France in 1843, has caused tremendous economic loss in animal husbandry for over one century. Scientists all over the world have been making efforts to investigate techniques to control this disease. Since the 1960s, the Chinese government has provided extraordinary financial support to fund studies on the biological and immunological properties of EIAV. During their investigations, Chinese scientists isolated a virulent strain that was quite different from strains isolated in other countries. Through passage on donkey luekocyte for many generations, this virulent strain was successfully attenuated. Using this attenuated virus as a vaccine strain, inoculated animals developed persistent and strong immunity against EIAV and were protected against Equine Infectious Anemia. The vaccine has been prepared in large scale since 1976 and used nation-wide since 1978. More than 70 million horses, mules, and donkeys have been vaccinated and Equine Infectious Anemia has been successfully controlled in China (Rongxian Shen, et al. Study on immunological methods of Equine Infectious Anemia, China Agricultural Science, vol. 4, 1–15, 1979).

EIAV is classified as a lentivirus of the Retroviridae family. In many aspects, such as its genomic organization, functional proteins and the regulatory mode of gene expression, EIAV shows great similarity to Human Immunodeficiency Virus (HIV), another lentivirus which is the cause of AIDS. (J. M. Coffin, The structure And Classification of Retroviruses, The Retroviridae, Vol. 1, p 19, edited by Jay A. Levy, Plenum Press). Moreover, there are extensive homologies in structure and function of reverse transcriptase, proteinase, envelope glycoprotein, and nucleoprotein between EIAV and HIV. Horses infected with EIAV manifest symptoms typical of lentiviral infection, including periodical fever, anemia with the decrease of erythrocytes and durative viremia. Thus, EIAV may serve as an important research model in investigating the infection mechanisms and the enzymatic functions of other lentiviruses (R. C. Montelaro et al, Equine Retroviruses, in: vol. 2, p 257).

With the development and widespread application of molecular biology since the 1970s, the genomic organization of EIAV has been intensively studied. Full-length genome sequences of EIAV from the standard (reference) virulent strain isolated in the USA (Wyoming strain), from another isolate in Japan (Goshum strain), and from several cell culture-adapted strains have all been registered in GenBank. None of these, however, are vaccine strains. Currently, the EIAV donkey leukocyte attenuated vaccine strain that was developed in China remains the only lentivirus vaccine strain in the world. It has been used in large scale and has been proven to be effective and safe over a long period of application (R. C. Montelaro, et al. in: Vaccine against Retroviruses, Vol. 4, P 605; R. C. Montelaro, et al. Equine Retroviruses, in: Vol. 2, P 257). The genomic sequence and organization of the EIAV vaccine strain has not been previously characterized. The characterization of the EIAV vaccine strain genomic sequence and structure will not only lay the foundation for refining the vaccine and preparing new genetic engineering EIAV vaccines, but also, more importantly, may provide a model for developing other lentivirus vaccines.

Therefore, the objects of the invention are to provide the full-length genomic sequence of the EIAV vaccine strain adapted to donkey leukocyte; the sequences of each functional genes and their putative amino acid sequences; and uses of these genes and their expression products.

SUMMARY OF THE INVENTION

The present invention relates to the full-length genomic sequence of the donkey leukocyte attenuated EIAV vaccine strain, including sequences of the main structural genes (gag, pol, env) and the regulatory genes (LTR, rev, s2, tat). The full-length sequence of this strain is 8258 bp long. The nucleotide sequence is shown in SEQ ID NO:1 (see below). In this full-length sequence, the 5'-terminal LTR sequence extends from position 1 to 325 and the 3'-terminal LTR spans from position 7922 to 8258. The gag gene occupies the sequence between 466 and 1926; the pol gene spans the sequence between 1689 and 5120; and the env gene extends from 5313 to 7904. The regulatory gene tat contains two exons: the first exon lies between positions 365 and 462 while the second spans from 5138 to 5276. Similarly, the regulatory gene rev also contains two exons: the first exon is found from position 5454 to 5546, while the second spans from position 7250 to 7651. The gene S2 lies between positions 5287 and 5493. The sequences of all these functional genes and their putative amino acid sequences are listed in SEQ ID NOs: 2 to 7 and SEQ ID NOs: 8 to 13, respectively. A genomic clone of the full-length gene sequence of EIAV donkey leukocyte attenuated vaccine strain was originally deposited to the China General Microbiological Culture Collection Center (CGMCC) on Apr. 19, 1999 with an accession number of CGMCC No. 0394. This deposit was transferred to an international deposit under Budapest Treaty on Apr. 19, 2000. As it is known by the skilled persons, the sequences shown in SEQ ID NOs: 1 to 7 may have some sequencing errors. If so, the deposited clone is the only data source.

DESCRIPTION OF THE PREFERRED EMBODIMENTS

The objects of the invention have been realized using the following techniques. Because the donkey leukocyte-adapted EIAV strain is in the form of a provirus during its replicative phase in vitro and is integrated into the chromosomes of donkey leukocyte, the chromosomal DNA of donkey leukocyte infected with attenuated EIAV was extracted and used as templates for PCR amplification. Briefly, the preliminary PCR amplifications were first carried out by using different primers that were designed based on the genomic sequences of reference EIAV virulent strains. These PCR products were then sequenced. Specific primers that matched the fragment sequence of attenuated EIAV were synthesized and used for another round of PCR amplification. Finally the different PCR products, representing different regions of attenuated EIAV genome, were respectively cloned and sequenced. The full-length sequence including structural genes (gag, pol and env) and regulatory genes (LTR, rev, S2 and tat) of EIAV vaccine strain was obtained.

The ORF of full-length sequence was analyzed with GCG software (Genetic Computer Group, Inc., Wisconsin, USA). The nucleotide and the deduced amino acid sequences of different structural and regulatory genes were identified in the full-length sequence.

Compared with the sequences of the reference EIAV virulent strains that were released by Genbank, the nucleotide sequence homologies between each gene of the vaccine strain and that of the reference strains were 73.46%–90.06%. The env, rev and S2 genes were among those with lower sequence homologies between the vaccine and reference strains. The homologies in nucleotide sequences between env, rev and S2 of the vaccine strain and those of the reference strains were 73.46%, 73.54% and 75.76%, respectively, and the homologies in amino acid sequences were 67.41%, 64.85% and 54.51%, respectively.

In addition, the secondary structures of the structural and regulatory proteins of EIAV vaccine strain were predicted using the GCG software. A significant difference was shown in secondary structures of the env and tat proteins between the vaccine and references strains. The quantities and the locations of α-helices, β-sheets and β-turns in many domains were quite different. There is a hydrophobic group at the C-terminal in the tat protein of the vaccine strain, a β-sheet in proximal region that forms a concentrated hydrophilic group, and 4 β-turns at N-terminal. In contrast, no hydrophobic groups are found at the C-terminal in the tat protein from the reference strains. Instead, there are loose random coils in proximal regions rather than a β-sheet, although 2 separate and distinct hydrophilic groups can be found. Moreover, many β-turns are present at the N-terminals. These differences between secondary structures may indicate functional differences. Based on these differences, we can modify the related genes and proteins of HIV and other lentivirus, and investigate the use of these modified strains as possible vaccines.

Moreover, it was also found through the sequence analysis that there are 19 potential N-linked glycosylation sites in env gene of the vaccine strain, whereas 23 potential N-linked glycosylation sites can be found in the same region of the reference strain.

The present invention serves as the first report within China and abroad which characterizes in detail the genomic organization (including structural and regulatory genes and the related proteins) of full-length genome of EIAV vaccine strain. This invention will guide attempts to develop the vaccine for immunoprophylaxis of chronic diseases caused by other lentivirus. The nucleotide sequence and the serological diagnostic reagents derived from the genes and proteins of EIAV vaccine strain can be used in the diagnosis of EIAV infection, the differentiation of infection by wild-type virus and inoculation of EIAV vaccine, and the development of new vaccines through genetic engineering. The gene sequence reported here can also be used for differentiating horses immunized with EIAV vaccine from those infected with the EIAV American strain, as described in Example 2 below. Finally, the full-length genome of the EIAV vaccine strain can be used to construct the gene transfer vector that is generally used in gene therapy. Since EIAV cannot cause illness to humans, the EIAV-based transfer vector can be used more widely and safely than other vectors, such as the vector derived from murine leukemia virus (MLV).

Figure 1:
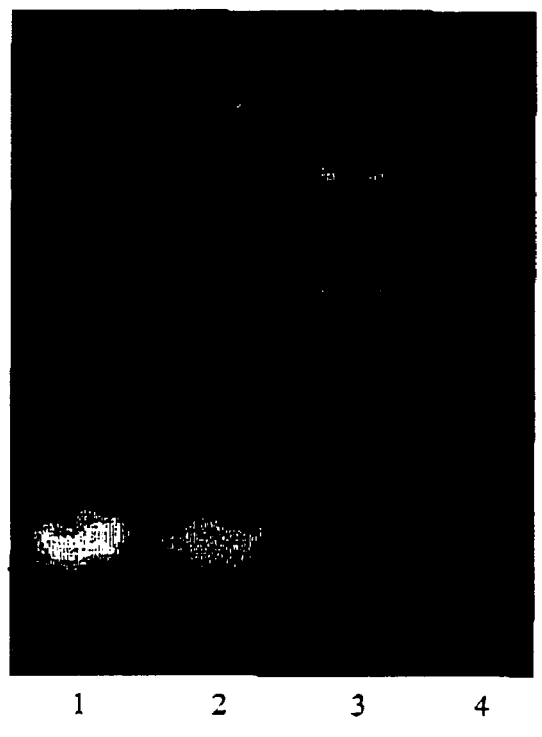
FIG. 1 shows the PCR amplification results of different templates using primer set I, as described in Example 2. Lanes 1 and 2 indicate the amplification results of total DNA from donkey leukocytes infected with the EIAV vaccine strain (~200 bp); Lane 3 is the DNA marker (pBR322/BstNI); Lane 4 is amplification results of total DNA from donkey leukocytes infected with the reference strain (Wyoming strain).

The invention will be illustrated with reference to the drawings and following examples.

EXAMPLE 1

Sequencing of the complete genome of Equine Infectious Anemia Virus (EIAV) donkey leukocyte attenuated vaccine A. Virus culture and extract of cell genome DNA The Equine Infectious Anemia Virus (EIAV) donkey leukocyte attenuated vaccine (Harbin Veterinary Research Institute, Harbin, China) was inoculated into healthy donkey leukocyte culture at 37° C. with 100% bovine serum (1 ml/$10^7$ cells). When cell pathological effect appeared, the supernatant was discarded, and the cell genome DNA was extracted using Qiagen Genomic DNA Kit (Qiagen, USA).

B. Amplifying, cloning and sequencing of different fragments of EIAV full-length genome The gp90 and 5' LTR genes of the invention were first amplified using primers designed according to the published sequences of Wyoming strains. Then, primers were designed according to the vested sequences to amplify the other ranges of the genome. The PCR products were subcloned into pGEM®-T Easy Vector (Promega) according to manufacturer's protocol. The restriction endonuclease EcoRI was used to identify recombination and ABI 377 DNA sequencer was used to sequence. Overlapping fragments of sequence were organized into a complete genome and every gene was identified by GCG software. The complete genome sequence is listed in SEQ ID NO. 1. Identified genes are presented in SEQ ID NO. 2–7. The following is concreted performance of different fragments:

(1) Fragment A(FA):
Amplified range: 5'LTR(1–320)
Primers and method:
First circle (SEQ ID NOS:14 and 15, respectively):
   Forward primer: LTR-F1 5'-GCGCGCGAATTCT-GTGGGGTTTTTATGAG-3'
   Backward primer: GR11 5'-AACCTTGCTGCTATGG-GAAT-3'
   Reaction system: 10×buffer ($Mg^{2+}$ 2 mM) 5 ul, dNTP (10 mM) 1 ul, LTR-F1 (20 uM) 1 ul, GR11 (20 uM) 1 ul, Taq polymerase (Promega) 1 ul (1 u), template 1 ul (200 ng), $H_2O$ 41 ul.
   Reaction program: 95° C. 5 min; then 94° C. 1 min, 52° C. 1 min, 72° C. 1.5 min, for 30 cycles followed by 72° C. 10 min.
Second circle (SEQ ID NOS:14 and 16, respectively):
   Forward primer: LTR-F1 5'-GCGCGCGAATTCT-GTGGGGTTTTTATGAG-3'
   Backward primer: LTR-R1 5'-CCCCCTCTAGATCTAG-GATCTGGAACAGAC-3'
   The reaction system was the same as the first circle except the primer and the template was replaced with 5 ul of the product from the first cycle.
   Reaction condition: 95° C. 5 min; then 94° C. 1 min, 55° C. 1 min, 72° C. 1 min, for 30 cycles followed by 72° C. 10 min.
Sequencing method: universal primer T7 was used.

(2) Fragment B (FB):
Amplified range: 115–1188
Primers (SEQ ID NOS:17 and 15, respectively) and method:
   Forward primer: 732 5'-ACCGCAATAACCGCATTTGT-GACG-3'
   Backward primer: GR11 5'-AACCTTGCTGCTATGG-GAAT-3'
   The reaction system is same as the first amplification cycle of FA (above) except that primer 732 and GR11 were used. The reaction condition was the same as the first amplification cycle of FA.
Sequencing method:
   Universal primers T7 and SP6 were used.

(3) Fragment C (FC):
Amplified range: 460–5254
Primers (SEQ ID NOS:18 and 19, respectively) used in the first cycle:
   Forward primer: P13 5'-GTAAGATGGGAGAC-CCTTTG-3'
   Backward primer: EVENR1 5'-ATGCTGACCATGT-TACCCCTT-3'
Primers (SEQ ID NOS:18 and 20, respectively) used in the second cycle:
   Forward primer: P13 5'-GTAAGATGGGAGAC-CCTTTG-3'
   Backward primer: EVENR2 5'-CAGATACTGAGGT-TGTCTTCCT-3'
Reaction system and condition:
   Expend™ Long Template PCR System (Boehringer Mannheim) was used according to the protocol (the buffer is buffer 3); The PCR product was subcloned into a vector at common restriction sites and sequenced with universal primers T7, SP6, and the RLR10.

Sequencing method:
   Initially, universal primers T7 and SP6 were used and the direction of gene insertion was decided. Then the primers named RTF1, RTR20, RTR40, and GF40 were designed and synthesized according to the vested sequence, so that the sequencing extended. By this means, the full-length sequence of a subcloned DNA fragment was obtained.
The DNA sequences of the primers (SEQ ID NOS:21 to 27, respectively) are as follows:
   T7 5'-TAA TC GAC TCA CTA TAG GGA GA-3'
   SP6 5'-CAT ACG ATT TAG GTG ACA CTA TAG-3'
   RTF1 5'-CCT CGA GGG AGA TGC ATA TTT C-3'
   RTR20 5'-CCC TCA TCT CAT CCA TGT T-3'
   RTR40 5'-GGT ATA GTG AAA TAT GCA TCT CC-3'
   GF40 5'-AAG TGA GGG ACA TCC GGC T-3'
   RLR10 5'-CTG TCC TCC CAT ACT TTC-3'

(4) Fragment D (FD):
Amplified range: (5222–6715)
Primers (SEQ ID NOS:28 and 29, respectively) and method:
   Forward primer: F70 5'-CCAACAAGGAAGGACAAC-CTC-3'
   Backward primer: R51 5'-AGACATAGTAGCGCTAG-CAG-3'
   The reaction system was the same as the first amplification cycle of FA, except that the primers F70 and R51 were used. The reaction condition was 95° C. 5 min; then 94° C. 1 min, 52° C. 1 min, 72° C. 2 min, for 30 cycles followed by 72° C. 10 min.
Sequence method:
   Primers T7 and SP6 were first used to sequence, and primer (SEQ ID NO:30) LTR20 was designed from the resulting sequence (5'-GCCTTAATGCAACAGTC-3'). The complete sequence was obtained from LTR 20.

(5) Fragment E (FE):
Amplified range: (6680–8174)
Primers (SEQ ID NOS:31 and 32, respectively):
   Forward primer: EF51 5'-GCTACTGCTATTGCT-GCTAG-3'
   Backward primer: LR3 5'-CTCAGACCGCAGAATCT-GAGT-3'
Reaction system and condition:
   Amplification was performed according to the protocol of Expend™ Long Template PCR System (Boehringer Mannheim) (Buffer 3 was used);
Sequence method:
   Universal primers T7 and SP6 were used.

(6) Fragment F (FF):
Amplified range: 3'LTR (7937–8251)
Primers (SEQ ID NOS:31 and 16, respectively) used in the first cycle:
   Forward primer: EF51 5'-GCTACTGCTATTGCT-GCTAG-3'
   Backward primer: LTR-R1 5'-CCCCCTCTAGATCTAG-GATCTGGAACAGAC-3'
Primers (SEQ ID NOS:14 and 16, respectively) used in the second cycle:
   Forward primer: LTR-F1 5'-GCGCGCGAATTCT-GTGGGGTTTTTATGAG-3'
   Backward primer: LTR-R1 5'-CCCCCTCTAGATCTAG-GATCTGGAACAGAC-3'
   The reaction system of the first cycle was similar to that of the first circle of Fragment A amplification, except that primers EF51 and LTR-R1 were used. The reaction condition is: 95° C. 5 min; then 94° C. 1 min, 52° C. 1 min, 72° C. 1.5 min, for 30 cycles followed by 72° C. 10 min.

The reaction system of the second cycle was similar to that of the first cycle mentioned above, except that primers LTR-F1 and LTR-R1 were used and 5 ul of amplified product of the first cycle was used as the template. The reaction condition is: 95° C. 5 min; then 94° C. 1 min, 55° C. 1 min, 72° C. 1 min, for 30 cycles followed by 72° C. 10 min.

Sequencing method:

Universal primer T7 was used.

EXAMPLE 2

Diagnosis methods distinguishing EIAV attenuated vaccine strain from American epidemic EIAV strains This example demonstrates the use of the gene sequences of the invention in detecting EIAV pathogen characteristics. It is useful to diagnose horses immunized by EIAV attenuated vaccine strain from those infected by the American epidemic EIAV strains.

Using the genomic sequence of the EIAV donkey leukocyte attenuated vaccine strain of this invention and the sequence of international standard strain Wyoming (Genebank Accession No. AF028232), the following primers (SEQ ID NOS:33 to 39, respectively) specific to EIAV donkey leukocyte attenuated vaccine strain were designed and synthesized.

| Primer name | Position | Sequence(5'-3') | Direction |
|---|---|---|---|
| CHF1369 | 1369 | GGACATCCGGCTGATATAAC | Forward |
| CHR1567 | 1567 | GACCAGCTAATCCTGCTTGA | Backward |
| CHR1553 | 1553 | GCTTGAAGTGCCTTGGCTAA | Backward |
| CHF5129 | 5129 | TCAGGAATCACCACCAGTCAG | Forward |
| CHR5610 | 5610 | GTTGTTGCCTCTCATACCAC | Backward |
| CHF1338 | 1338 | AGACAGATTGCTGTCTC | Forward |
| CHR1572 | 1572 | CATAGGACCAGCTATC | Backward |

PCR was performed on different templates including total DNA from donkey leukocytes inoculated with the EIAV attenuated vaccine and from donkey leukocytes inoculated with international standard strain Wyoming. Taq DNA polymerase was purchased from PROMEGA Corp. PCR system includes 10×buffer 5 ul, 2.5 mM $MgCl_2$ 1 ul, dNTP (2.5 mM) 1 ul, primer 1 (20 uM) 1 ul, primer 2 (20 uM) 1 ul, Taq polymerase (Promega) 1 ul (2 u), $H_2O$ 34.6 ul, template 2 ul. Primer 1 and primer 2 were combined as following group:

Group I: CHF1369+CHR1567 (Product is about 200 bp in length)

Group II: CHF1369+CHR1553 (Product is about 190 bp in length)

Group III: CHF5129+CHR5610 (Product is about 380 bp in length)

Group IV: CHF1338+CHR1572 (Product is about 220 bp in length)

Reaction conditions* 95° C. 5 min; then 94° C. 40 s, 50° C. 30 s, 72° C. 30 s, for 30 cycles followed by 72° C. 10 min.

Figure 2:
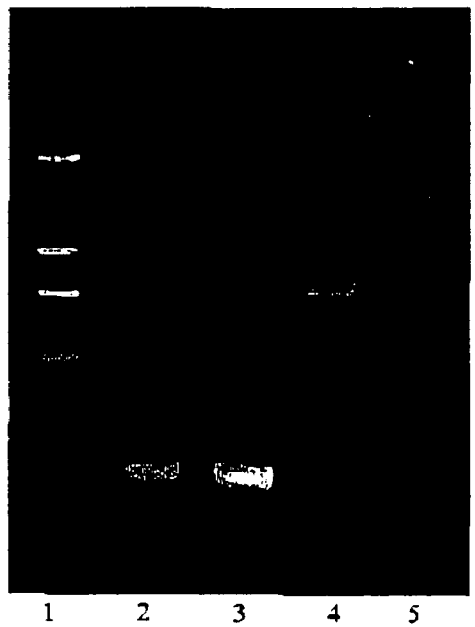
FIG. 2 shows the PCR amplification results of different templates using primer set II, as described in Example 2. Lane 1 is the DNA marker (DL2000, TaKaRa); Lanes 2 and 3 are the amplification results of total DNA from donkey leukocytes infected with the EIAV vaccine strain (~190 bp); Lane 4 indicates the amplification results of total DNA from donkey leukocytes; Lane 5 shows the amplification results of total DNA from donkey leukocytes infected with the reference strain (Wyoming strain).
Figure 3:
FIG. 3 shows the PCR amplification results of different templates using primer set III, as described in Example 2. Lane 1 is DNA marker (pBR322/BstNI); Lane 2 shows amplification results of total DNA from donkey leukocytes infected with the reference strain (Wyoming strain). Lanes 3 and 4 are the amplification results of total DNA from donkey leukocytes infected with EIAV vaccine strain (~380 bp).
Figure 4:
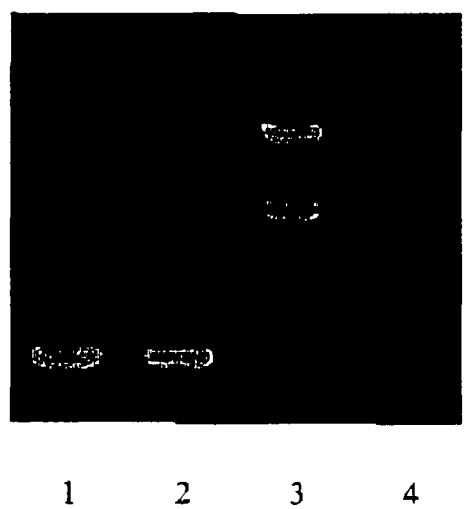
FIG. 4 shows the PCR amplification results of different templates using primer set IV, as described in Example 2. Lanes 1 and 2 are the amplification results of total DNA from donkey leukocytes infected with EIAV vaccine strain (~220 bp); Lane 3 is DNA marker (pBR322/BstNI); Lane 4 is amplification results of total DNA from donkey leukocytes infected with the reference strain (Wyoming strain).

The results were analyzed by agarose gel electrophoresis. It is demonstrated that the use of different primer groups leads to specific amplification products from the total DNA of the donkey leukocyte inoculated with the EIAV attenuated vaccine but not from DNA from donkey luekocyte inoculated with the international standard strain Wyoming under the same conditions. See FIGS. 1–4.

What is claimed is:

1. An isolated polynucleotide comprising the nucleotide sequence as set forth in SEQ ID NO:1, wherein said polynucleotide encodes the full-length provirus genome of Equine Infectious Anemia Virus Donkey Leukocyte Attenuated Vaccine strain, wherein nucleotide 1 to 325 of SEQ ID NO:1 is the 5'LTR; nucleotide 7922 to 8258 is the 3'LTR; nucleotide 466 to 1926 is the gag gene; nucleotide 1689 to 5120 is the pol gene; nucleotide 5313 to 7904 is the env gene; nucleotide 365 to 462 is the first exon of tat gene; nucleotide 5138 to 5276 is the second exon of tat gene; nucleotide 5454 to 5546 is the first exon of rev gene; nucleotide 7250 to 7651 is the second exon of rev gene; and nucleotide 5287 to 5493 is the S2 gene.

2. A method for the manufacture of a recombinant vector, comprising the step of inserting the polynucleotide of claim 1 in a suitable vector.

3. An isolated polynucleotide comprising the sequence contained in the deposit under CGMCC deposit number 0394.

* * * * *